United States Patent [19]
Rocafort

[11] Patent Number: 5,637,296
[45] Date of Patent: Jun. 10, 1997

[54] LOW VOC HAIR SPRAY RESIN COMPOSITION OF IMPROVED SPRAY PROPERTIES

[75] Inventor: Colleen M. Rocafort, Lake Hiawatha, N.J.

[73] Assignee: ISP Investments Inc., Wilmington, Del.

[21] Appl. No.: 298,738

[22] Filed: Aug. 31, 1994

[51] Int. Cl.$^6$ ............................................. A61K 7/11
[52] U.S. Cl. .................. 424/70.11; 424/47; 424/70.15; 424/70.16; 424/DIG. 1; 424/DIG. 2; 514/957; 132/202
[58] Field of Search .................. 404/47, DIG. 1, 404/DIG. 2, 78.02, 70.11, 70.16, 70.15; 514/957; 132/209

[56] References Cited

U.S. PATENT DOCUMENTS 5,126,124 6/1992 Tazi et al. ............................ 424/47
5,158,762 10/1992 Pierce ................................... 424/47

OTHER PUBLICATIONS

Oteri, R. et al. (1991). Cosmetics & Toiletries, vol. 106, pp. 29–34.
Martino, G. T. et al. (1992) Cosmetics & Toiletries, vol. 104, pp. 34–39.

*Primary Examiner*—Raj Bawa
*Attorney, Agent, or Firm*—Marilyn J. Maue; Walter Katz; Joshua J. Ward

[57] ABSTRACT

This invention relates to a 0.5 to 7 wt. % solids hair fixative composition having superior moisture resistant hold and minimal tack duration which provides a stiff film on artificial or human hair and superior hair combability, which composition essentially contains a resin mixture of (a) a terpolymer derived from about 17 to about 30 wt. % N-vinyl pyrrolidone, from about 60 to about 80 wt. % N-vinyl caprolactam and from about 3 to about 6 wt. % di-$C_1$-$C_4$ alkyl amino-$C_1$-$C_4$alkyl-acrylate or methacrylate having a number average molecular weight of between about 20,000 and about 200,000 and (b) a N-vinyl pyrrolidone/vinyl acetate copolymer having a number average molecular weight of between about 10,000 and about 100,000; combined in a weight ratio of 1.4–6:1 (a) to (b). In the present composition, the vinyl acetate moiety of the N-vinyl pyrrolidone/vinyl acetate copolymer interacts with resin (a) to reinforce stiffness and holding properties under conditions of extremely high humidity and materially lowers the duration of tackiness during drying.

18 Claims, No Drawings

LOW VOC HAIR SPRAY RESIN COMPOSITION OF IMPROVED SPRAY PROPERTIES

BACKGROUND OF THE INVENTION

N-vinylpyrrolidone homopolymers and homopolymeric alkyl substituted N-vinylpyrrolidone derivatives in the K 15 to 90 range have been employed as hair fixatives since these film forming polymers are nontoxic and possess some hair holding ability. Although improvements in the later property have been achieved through the development of N-vinyl lactam terpolymers, their incorporation in hair sprays has not provided the degree of stiffness needed for hair setting. Accordingly, several N-vinyl pyrrolidone terpolymer mixtures have been employed to combine stiffness and hold in pump spray and aerosol hair setting formulations. For example U.S. Pat. No. 5,158,762 utilizes mixtures of N-vinyl pyrrolidone, N-vinyl caprolactam and dimethylaminoethyl-methacrylate terpolymer (e.g. GAFFIX® VC-713, supplied by International Specialty Products) and polyhydroxylated sulfate ester salts; however, these compositions are not altogether satisfactory in that they lack strong holding power and desired stiffness under high humidity conditions. Additionally, tack duration is extended and the mixture exibits wet hair comb drag resulting in poor combability.

U.S. Pat. No. 5,126,124 employs mixtures of relatively high and low molecular weight resins, e.g. GAFFIX® VC-713 and polyvinylpyrrolidone to achieve acceptable stiffness and holding power, although tackiness at high humidity and low combability remain unsolved and troublesome problems.

While GAFFIX alone has been proposed as a hair fixative having good conditioning and high humidity holding power (HHCR), as in U.S. Pat. No. 4,521,404, the terpolymer fails to provide the degree of stiffness required for current hair sprays. From the teachings in the art, it appears that active components combined with vinyl lactam terpolymers in a given hair spray mixture for the purpose of solving or minimizing one problem, generally result in creating or exacerbating another. Hence, the combinations of individual active components in a vinyl lactam polymer mixture is highly unpredictable. Particularly, it would be expected that the excellent holding properties of N-vinyl lactam/aminoacrylate terpolymers would be proportionately diminished by dilution with hygroscopic polymeric additives having little or no holding power in aqueous solutions.

Accordingly, it is an object of this invention to provide a specific resin mixture derived from four monomeric components as the active ingredients in a hair spray formulation having improved hold and stiffness under very high humidity conditions while increasing combability and minimizing tackiness during drying on the hair.

Another object is to provide a hair fixative which possesses the above beneficial properties and which forms a clear, colorless, non-flaking film which is readily removed with shampoo and does not cause build up on hair fibers.

Still another object is to provide an economical hair spray composed of resins which are commercially available but which have opposing hair treating properties.

These and other objects of the invention will become obvious from the following description and disclosure.

DEFINITIONS

For the purposes of this disclosure:
1. The active hair fixative resin is a mixture of N-vinyl pyrrolidone/N-vinyl caprolactam/dialkylaminoalkyl acrylate or methacrylate terpolymer and N-vinyl pyrrolidone/vinyl acetate copolymer.
2. The hair spray concentrate is the active hair fixative resin mixture in an organic carrier wherein the concentration of the resin mixture is between about 25 and about 50 wt. %.
3. The low VOC (volatile organic compounds) pump hair spray composition is the 80–95 wt. % water or hydroalcoholic solution or suspension of the terpolymer and copolymer resin mixture containing 0.5–7% solids.
4. The low VOC aerosol hair spray composition is the 0.5–7% solids composition of the terpolymer and copolymer mixture in between about 45 and about 75 wt. % aqueous alcohol, between about 25 and about 50 wt. % aerosol propellant and neutralizer.

THE INVENTION

In accordance with this invention there is provided an improved hair fixative composition which comprises an aqueous, low VOC, 0.5 to 7 wt. % solids mixture consisting essentially of, as the active hair fixative ingredients, (a) a terpolymer of from about 17 to about 30 wt. % N-vinyl pyrrolidone, from about 60 to about 80 wt. % N-vinyl caprolactam and from about 3 to about 6 wt. % di-$C_1$ to $C_4$ alkyl amino $C_1$ to $C_4$ alkyl-acrylate or methacrylate having a number average molecular weight of between about 20,000 and about 200,000 and (b) a N-vinyl pyrrolidone/vinyl acetate copolymer having a number average molecular weight of between about 10,000 and about 100,000, combined in a weight ratio of 1.4–6:1 (a) to (b).

Hygroscopic copolymer (b) is composed desirably of from about 25 to 75 parts vinyl pyrrolidone (VP) and 75 to 25 parts by weight vinyl acetate (VA); preferably a 60–70/40–30 mixture, and most preferably a 70/30 monomer proportion. This copolymer is most beneficially combined with terpolymer (a) in a weight ratio of 1:2–3.5 copolymer (VP/VA) to terpolymer which provides a hair fixative mixture formulation exhibiting short tack duration and excellent combability coupled with superior hair hold and stiffness in humid atmospheres. The terpolymer is referred to herein as VP/VCL/AA or VP/VCL/AA terpolymer.

The preferred VP/VCL/AA terpolymers of this invention are those wherein the aminoacrylate monomer is a dimethylamino $C_1$ to $C_3$ alkylmethacrylate, dimethylaminoethyl-methacrylate being most preferred. The terpolymer component of the mixture can be introduced in the form of a powder or as an alcohol or aqueous alcohol solution containing from about 25 to about 65% terpolymer. An example of a most preferred commercially available VP/VCL/AA terpolymer solution is GAFFIX® VC-713, 37% terpolymer in $C_2$ to $C_4$ alkanol e.g. ethanol. An example of the commercially available terpolymer powder is H2OLD EP-1 powder, both supplied by International Specialty Products.

Concentrates of the present hair fixative mixture are prepared in from about 50 to about 75 wt. % liquid carrier, more desireably from about 60 to about 68 wt. % liquid carrier. The concentrate can be subsequently diluted before use with the same or a different liquid. Suitable liquid carriers employed herein include lower $C_1$ to $C_4$ alcohols, heptane, cyclohexane, methylethyl ketone and aqueous solutions of the same and mixtures of carriers.

The use of the present concentrates in the final formulation of a hair spray are diluted to form a liquid solution, containing from about 25 to about 50 wt. %, preferably from about 35 to about 40 wt. % concentrate to provide a low VOC hair spray having not more than 55% volatiles.

Hair spray concentrates of the invention can be prepared as solutions, dispersions or suspensions, more desirably from liquids containing from about 30 to about 60 wt. %, preferably 35 to 45 wt. %, water and from about 70 to about 40 wt. %, preferably 65 to 55 wt. %, lower alkanol, particularly ethanol or isopropanol, which aqueous mixtures are suitable for use in pump or aerosol hair sprays.

Since water is known to plasticize vinylpyrrolidone in VP/VA copolymer, the presence of this copolymer in the above mixture would be expected to significantly lower humidity hold resistance of the terpolymer. Conversely, it is now discovered that the holding power of the terpolymer in the final hair spray is not reduced and that the desired degree of stiffness can be achieved for hair setting in the presence of up to about 40% water by the use of the present resin mixture.

When used in a pump spray formulation, the concentrate need not be neutralized, although up to about 0.5 wt. % of a conventional neutralizing agent can be employed if desired without detriment. However, when used in an aerosol spray, the composition contains between about 0.05 and about 0.5% of neutralizer to obtain a clear solution having a pH of 7–10, preferably 8–9.5. Examples of such neutralizing agents include organic and inorganic compounds such as sodium hydroxide, ammonium hydroxide, aminomethylpropanol, potassium hydroxide, dodecylamine, triethanolamine and the like and mixtures thereof. When used as an aerosol spray, between about 50 and about 80 wt. %, preferably between about 60 and about 70 wt. % of the concentrate composition can be mixed with from about 20 to about 50 wt. %, usually from about 30 to about 40 wt. %, of a conventional propellant such as butane, propane, isopropanol, nitrous oxide, carbon dioxide, dimethylether, difluoroethane, etc and mixtures thereof.

In addition to the above components, the hair fixative mixture of this invention may optionally contain up to 3 wt. % (based on total composition) of non-active excipients such as a surfactant, a preservative, a corrosion inhibitor, a conditioner, a hair curling agent, a hair coloring agent and/or other additives commonly employed to enhance the physical properties of the formulation. Examples of such excipients include PEG-75 lanolin; $C_{12-15}$ alkyl lactates; quaternary hydroxylated amide halides, e.g. mink amidopropyl dimethyl 2-hydroxyethyl ammonium chloride, gluconamido dimethyl 2-hydroxyethyl ammonium chloride and myristyl acetate ammonium chloride; diisopropyl adipate, polypropylene glycol-polyethylene glycol lanolin oil; lauramide diethyl amine; acetyl triethyl citrate, dimethicone copolyol; PEG amino glycerides; methyl ethyl amine borate; methyl isopropylamine borate; ammonium hydroxide; nitromethane; amino methyl propanol; tridecyl neopentanoate; myristyl lactate; isodecyl oleate; etc. and mixtures thereof.

In addition to the above desirable properties, the present hair sprays possess excellent stability and spray characteristics evident as a fine mist with no clogging of the spray nozzle. They also provide a clear film on the hair fibers which is easily removed by shampooing to avoid hair build-up and resist flaking on the hair.

The present hair fixative concentrates are economically prepared by simply adding the VP/VA copolymer resin, either as a powder or as a solution or dispersion, to an alcoholic solution of the VP/VCL/AA terpolymer after the addition of the desired amounts of water and/or alcohol and agitating the resulting dispersion or solution until a uniform mixture concentrate is attained. This is accomplished under ambient temperature or a temperature of up to about 27° C. Within a period of from about 10 minutes to about 1 hour, more often within 15 to 30 minutes, an intimate blend or dispersion of the resin mixture is obtained. For use in a pump spray, the final formulation contains from about 80 to about 95 wt. % liquid solvent; whereas the final formulation of an aerosol contains from about 45 to about 75% liquid solvent, allowing for the addition of propellant to the concentrate.

The copolymer in the above process can be employed as a 10 to 50% solution in a suitable solvent such as a $C_2$ to $C_4$ alcohol or as a dispersion in another solvent such as water or aqueous alcohol. The same or a different solvent within the above list can be employed for the terpolymer. Alternatively, the copolymer can be added as a dry powder and sprinkled into the terpolymer solution during the preparation of the concentrate.

Having generally described the invention, reference is now had to the accompanying examples which illustrate comparisons with prior hair sprays or preferred embodiments of the present invention of which the later are not to be construed as limiting to the scope of the invention more broadly set forth above and in the appended claims.

EXAMPLES 1–4

The following compositions of the invention were prepared in a stainless steel mixing vessel and mixed at ambient temperature for 20 minutes with a turbine agitator.

| Example Component | 1 | 2 | 3 | 4 |
|---|---|---|---|---|
| | | Weight % | | |
| GAFFIX ® VC-713 (37% active in ethanol) | 11.00 | 13.50 | — | — |
| H2OLD EP-1 powder 99.97% active | — | — | 4.00 | 4.00 |
| VP/VA W-735 (50% active in water) | 2.00 | 4.00 | 2.00 | 2.00 |
| Excipients | — | — | 0.07 | 0.27 |
| Propellant | — | — | — | 35.00 |
| Total Ethanol | 48.07 | 46.49 | 55.00 | 20.00 |
| Total Water | 38.93 | 36.01 | 38.93 | 38.73 |

Comparative Examples 5–13

The following hair sprays were prepared in the manner set forth in the preceding examples.

| Ex. No. | GAFFIX VC-713 | H2OLD EP-1 | COMPONENTS PVP K-30 | PVP K-15 | PVP K-90 | Solvent | Water | Excipient |
|---|---|---|---|---|---|---|---|---|
| 5 | — | 4.00 | 0.50 | — | — | 55.00 | 40.43 | 0.07 |
| 6 | 1.00 | — | 0.50 | — | — | 48.07 | 40.43 | — |
| 7 | 13.50 | — | 0.50 | — | — | 46.49 | 39.51 | — |
| 8 | 11.00 | — | — | — | 0.40 | 43.60 | 45.00 | — |

| Ex. No. | AQ 38S[1] | AQ 55S[1] | GANTREZ® AN-119[2] | LOVOCRYL 47[3] | DIAHOLD[4] | Excipient | Solvent | Water |
|---|---|---|---|---|---|---|---|---|
| 9 | 4.00 | — | — | — | — | — | 55.00 | 41.00 |
| 10 | — | 4.00 | — | — | — | — | 55.00 | 41.00 |
| 11 | — | — | 4.00 | — | — | 0.25 | 55.00 | 40.75 |
| 12 | — | — | — | 4.50 | — | 1.33 | 55.00 | 39.17 |
| 13 | — | — | — | — | 4.00 | — | 55.00 | 41.00 |

[1]$SO_3Na$ - containing polyols of diglycol isophthalates
[2]Methyl vinyl ether/maleic anhydride copolymer having 1.72 intrinsic viscosity
[3]A hydrophobic acrylic resin
[4]An anionic amine salt of a polymeric methacrylate mixture Comparative Examples—Hair Spray Properties The above stable hair spray compositions 1.20 ml. were tested by spraying 4% solids solutions on 2.0 g. swatches of human hair and observing the results for high humidity curl retention. All other tests, except hardness, employed 3.5 g. hair swatches. Film hardness was evaluated by application to a glass plate by drawing down a 0.03 inch film, allowing it to dry and evaluating by the standard pencil hardness test.

TABLE I

| Example No. | 1 | 2 | 3 | 4 | 5 | 6 | 7 |
|---|---|---|---|---|---|---|---|
| Film Hardness | 2H | H | H | HB | 4H | 4H | H |
| pH |  |  |  |  |  |  |  |
| Pump Spray | 8.8 | 9.3 | 9.0 | 8.9 | 9.3 | 8.7 | 8.9 |
| Aerosol spray | 9.3 | 9.3 | 9.2 | 8.9 | 9.4 | 9.3 | 9.0 |
| Hold 90% humidity |  |  |  |  |  |  |  |
| % at 90 mins | 94.32 | 95.38 | 98.94 | 85.55 | 96.43 | 93.62 | 97.35 |
| % at 4 hours | 94.32 | 91.26 | 93.75 | 74.03 | 90.86 | 92.34 | 96.02 |
| Duration of Tack (seconds) | 28 | 36 | 44 | 36 | 25 | 34 | 38 |
| Film Stiffness | 7.4 | 7.4 | 8.8 | 7.0 | 8.8 | 8.0 | 8.6 |
| Non-flaking | 9.4 | 9.6 | 9.0 | 9.0 | 9.2 | 9.0 | 8.4 |
| Combability | 7.8 | 8.4 | 4.2 | 4.8 | 5.6 | 7.0 | 5.8 |
| Dry Time (sec) | 80 | 82 | 80 | 66 | 76 | 73 | 76 |
| Spray Pattern inches | 3–3.5 | 3–3.5 | 3 | 3.5 | 3 | 3–3.5 | 3–3.5 |

| Example No. | 8 | 9 | 10 | 11 | 12 | 13 |
|---|---|---|---|---|---|---|
| Film Hardness | 4H | H | 3H | 8H | 2B | 3B |
| pH |  |  |  |  |  |  |
| Pump Spray Hold 90% humidity | 8.31 | — | — | 3.92 | — | — |
| % at 90 mins | 96.58 | 15.76 | 29.73 | 95.54 | 20.39 | 9.6 |
| % at 4 hours | 96.58 | 10.96 | 23.42 | 44.64 | — | — |
| Duration of Tack (seconds) | 30 | 12 | 12 | 94 | 30 | 27 |
| Film Stiffness | 9 | 6 | 5 | 9 | 2 | 3 |
| Non-flaking | 4 | 10 | 10 | 7 | 9 | 9 |
| Combability | 4 | 7 | 9 | 7 | 9 | 8 |
| Dry Time (sec) | — | 28 | 38 | 90 | 95 | 100 |

TABLE I-continued

| Spray Pattern inches | 3 | 3 | 3 | 3 | 3 | 3 |
|---|---|---|---|---|---|---|

PROCEDURE FOR PREPARING HAIR SPRAY COMPOSITIONS OF INVENTION

A. Pump Spray

The pump hair spray compositions of the invention were prepared by first dissolving the terpolymeric resin in an ethanol solution, and where needed for clarity, including a neutralizing agent. After, the requisite amount of water was added followed by gradually sifting in the VP/VA resin. The composition then was packaged into a high density polyethylene bottle fitted with a suitable pump actuator, here employed a pump sprayer (160 ml) with 0.018×0.010 inch deep actuator (SEAQUIST EUROMIST II).

B. Aerosol Compositions

The aerosol hair spray resin compositions of the invention, as illustrated by Example 4, were prepared from 65% by weight of the concentrate of the pump spray formulation of Example 1 and a 35% by weight of dimethylether propellant.

The above examples illustrate the uniqueness of the present hair fixative in satisfying all requirements of a hair spray composition, including stiffness, hold, combability, resistance to flaking, low tack duration, fast drying, elimination of hair build-up and clarity. Many other valuable properties will become apparent upon use of the present compositions.

What is claimed is:

1. A hair fixative resin concentrate consisting essentially of a mixture of (a) a terpolymer having a number average molecular weight of between about 20,000 and about 200,000 consisting of from about 17 to about 30 wt. % N-vinyl pyrrolidone, from about 60 to about 80 wt. % N-vinyl caprolactam and from about 3 to about 6 wt. % di-$C_1$ to $C_4$ alkylamino $C_1$ to $C_4$ alkylacrylate or methacrylate and (b) a 25–75 parts by weight N-vinyl pyrrolidone/75–25 parts by weight vinyl acetate copolymer having a number average molecular weight between about 10,000 and about 100,000; combined in a weight ratio of from about 1.4 to about 6 parts (a) to 1 part (b); said mixture dissolved or dispersed in at least 50% of a liquid solvent, based on said resin mixture, said liquid solvent selected from the group consisting of water, a $C_1$ to $C_4$ alcohol, heptane, cyclohexane, methylethyl ketone and mixtures thereof.

2. The concentrate of claim 1 wherein said dialkylamino alkyl methacrylate of said terpolymer is dimethylamino $C_1$ to $C_3$ alkyl methacrylate.

3. The concentrate of claim 1 wherein said copolymer is 25 to 75 parts by weight N-vinyl pyrrolidone and 75 to 25 parts by weight vinyl acetate.

4. The concentrate of claim 3 wherein the copolymer is 60 to 70 parts by weight N-vinyl pyrrolidone and 40 to 30 parts by weight vinyl acetate.

5. The concentrate of claim 1 wherein said liquid solvent is alcohol or an aqueous alcohol solution and said concentrate contains between about 25 and about 50 wt. % of the resin mixture.

6. The concentrate of claim 1 which additionally contains from 0 to about 3% based on total composition, of an excipient selected from the group consisting of a surfactant, a neutralizing agent, a preservative, a corrosion inhibitor, a hair conditioner, a hair curling agent, a hair coloring agent and mixtures thereof.

7. The concentrate of claim 1 wherein the weight ratio of (a) to (b) is 2–3.5:1.

8. A low VOC pump hair spray composition containing the concentrate of claim 1, between about 80 and about 95 wt. % total liquid solvent and between about 0.5 and about 7 wt. % solids in said liquid solvent.

9. An aerosol hair spray composition containing the concentrate of claim 1, between about 45 and about 75 wt. % total liquid solvent, between about 25 and about 50 wt. % propellant and 0–3% excipients.

10. The spray composition of claim 8 which contains a mixture of about 3–7 wt. % terpolymer and about 1–3 wt. % copolymer in at least about 90% aqueous $C_1$ to $C_4$ alcohol solution.

11. The aerosol spray of claim 9 which contains a mixture of about 3–5 wt. % terpolymer and about 1–2 wt. % copolymer, about 30–40 wt. % propellant in about 55–70 wt. % aqueous $C_1$ to $C_4$ alcohol solution to form 100% composition.

12. The process of preparing the concentrate of claim 1 which comprises (a) forming a solution or dispersion of said terpolymer resin in a liquid solvent, (b) gradually adding copolymer resin to said terpolymer solution or dispersion, (c) agitating the resulting mixture until a uniform composition is obtained and (d) diluting the resin composition with a liquid solvent to a concentration of from about 25 to about 50 wt. % total resin.

13. The process of claim 12 wherein said concentrate is mixed with a liquid solvent to form a low VOC hair spray composition containing from about 0.5 to 7 wt. % active hair fixative.

14. The process of claim 12 wherein said concentrate is diluted to a concentration of from about 80 to about 95 wt. % liquid solvent to form a low VOC pump hair spray composition to form a hair spray composition containing from about 0.5 to about 7 wt. % solids.

15. The process of claim 12 wherein up to about 3% of a non-active excipient selected from the group consisting of a surfactant, a neutralizing agent, a preservative, a corrosion inhibitor, a hair conditioner, a hair curling agent, a hair coloring agent and mixtures thereof is added to the concentrate.

16. The process of claim 12 wherein between about 20 and about 50 wt. % propellant and aqueous alcohol solution is added to the concentrate to form a low VOC aerosol spray composition containing from about 0.5 to about 7 wt. % solids.

17. The process of claim 12 wherein said terpolymer is derived from the polymerization of N-vinyl pyrrolidone, N-vinyl caprolactam and dimethylamine $C_2$ to $C_3$ alkyl methacrylate monomers.

18. The process of claim 12 wherein said liquid solvent is $C_1$ to $C_4$ alcohol, water or an aqueous solution of said alcohol.

\* \* \* \* \*